United States Patent [19]
Hergert

[11] Patent Number: 5,289,007
[45] Date of Patent: Feb. 22, 1994

[54] SHEET BREAK DETECTOR APPARATUS

[75] Inventor: Richard R. Hergert, Rockton, Ill.

[73] Assignee: Beloit Technologies, Inc., Wilmington, Del.

[21] Appl. No.: 888,954

[22] Filed: May 26, 1992

[51] Int. Cl.$^5$ .................. G08B 21/00; G01N 33/34
[52] U.S. Cl. .................................. 250/341; 250/340; 340/675
[58] Field of Search .............. 340/675; 250/340, 341

[56] References Cited

U.S. PATENT DOCUMENTS

| | | | |
|---|---|---|---|
| 3,906,232 | 9/1975 | Meihofer | 250/341 |
| 4,239,562 | 12/1980 | McLean | 156/64 |
| 5,019,710 | 5/1991 | Wennerberg et al. | 250/341 |

Primary Examiner—Constantine Hannaher
Attorney, Agent, or Firm—Dirk J. Veneman; Raymond W. Campbell; David J. Archer

[57] ABSTRACT

A sheet break detector apparatus is disclosed for detecting a break in a sheet disposed contiguously between an upstream and a downstream felt of a paper machine dryer section. The detector apparatus includes an infrared light emitter disposed adjacent to the sheet disposed between the felts for emitting a beam of infrared light towards the sheet moving contiguously between the felts. An infrared light receiver is disposed on an opposite side of the felts relative to the emitter for receiving the beam in the absence of the sheet, the beam being blocked by the presence of the sheet while the felts permit the passage therethrough of the beam. A transmitter is connected to the receiver for transmitting a signal from the receiver in the absence of the sheet. An alarm is connected to the transmitter such that in the event of sheet break, the beam of light is received by the receiver and the signal is transmitted to the alarm so that an alarm signal is generated, indicating that a sheet break has occurred.

8 Claims, 1 Drawing Sheet

SHEET BREAK DETECTOR APPARATUS

BACKGROUND OF THE INVENTION

1. Field Of The Invention

The present invention relates to a sheet break detector apparatus. More specifically, the present invention relates to a sheet break detector apparatus for detecting a sheet break in a transfer of a paper machine dryer section.

2. Information Disclosure Statement

In the operation of a typical papermaking machine dryer section, the web or sheet of paper extending therethrough may break eight or more times a day.

When a web breaks, it is essential that such breakage be detected as soon as possible so that the web can be rethreaded.

Typically, when a break occurs in a dryer section, the loss of production amounts to around $40,000 per hour.

Furthermore, if a web breakage is not readily detected, there exists the problem of two dryer felts rubbing against each other, particularly in the case of a web transfer section in a Bel-Champ TM dryer section in which the web may be transferred without open draw between respective dryer sections. A Bel-Champ TM dryer section is taught in U.S. Pat. No. 4,934,067 assigned to Beloit Corporation.

Such scuffing between adjacent felts may result in burning one or the other of the felts.

Felts typically cost in the region of $40,000 each, and the downtime required to replace a felt may be several hours.

Accordingly, the present invention provides a simple means for quickly detecting a web breakage.

In the prior art, optical detecting systems have been employed, which include a photoelectric sensor. However, such photoelectric sensors require the provision of a felt having a color difference relative to the sheet or web in order for such photoelectric sensors to work efficiently.

Also, sensors have been provided which sense the vacuum level existing within a vacuum roll disposed upstream or downstream relative to the double felted web transfer section.

Such vacuum sensors do not work effectively if only a low vacuum exists within the vacuum transfer roll.

Also, such vacuum sensors would not operate if a grooved roll was substituted for the typical vacuum transfer roll.

Applicant has discovered that a beam of infrared light will freely pass through at least two dryer felts, but that such infrared beam will be blocked when a sheet or web of paper is interposed between the respective dryer felts.

Therefore, the present invention provides a sheet break detector apparatus which overcomes the aforementioned disadvantages of the aforementioned prior art arrangements and provides a detector apparatus which makes a considerable contribution to the art of drying a web in a paper machine dryer section.

A primary objective of the present invention is the provision of a sheet break detector apparatus which works efficiently regardless of the color of the dryer felt.

Another object of the present invention is the provision of a sheet break detector apparatus which operates independently of the existence of a vacuum applied to a vacuum transfer roll.

Other objects and advantages of the present invention will be readily apparent to those skilled in the art by a consideration of the detailed description contained hereinafter, taken in conjunction with the annexed drawings.

SUMMARY OF THE INVENTION

The present invention relates to a sheet break detector apparatus for detecting a break in a sheet which is disposed contiguously between an upstream and a downstream felt of a paper machine dryer section. The apparatus includes an infrared light emitter means which is disposed adjacent to the sheet, which is disposed between the felts for emitting a beam of infrared light towards the sheet moving contiguously between the felts. An infrared light receiver is disposed on an opposite side of the felts relative to the emitter means for receiving the beam in the absence of the sheet. The beam is blocked by the presence of the sheet while the felts permit the passage therethrough of the beam.

Transmitter means is connected to the receiver for transmitting a signal from the receiver in the absence of the sheet.

Alarm means are connected to the transmitter means such that in the event of a sheet break, the beam of light is received by the receiver, and the signal is transmitted to the alarm means so that an alarm signal is generated, indicating that a sheet break has occurred.

In a more specific embodiment of the present invention, the infrared light emitter means includes an infrared light source generator for generating infrared light and a fiber-optic means extending from the generator for guiding the infrared light from the generator. The emitter means also includes a lens which is disposed at an opposite end of the fiber-optic means relative to the generator for concentrating the light generated by the generator.

Additionally, the detector apparatus includes air purge means which are disposed adjacent to the lens for directing a curtain of air past the lens for cleaning the lens.

The infrared light receiver includes an optical means for concentrating the beam emitted from the emitter means, said beam passing through the felts in the absence of the sheet.

The transmitter means includes a light guide which is disposed closely adjacent to the optical means for guiding the beam, which is concentrated by the optical means. The arrangement is such that the signal is a light signal which is transmitted in the absence of the sheet between the felts.

The break detector apparatus also includes an air nozzle which is disposed closely adjacent to the optical means for blowing air across the optical means in order to remove any contamination therefrom, thereby optimizing the light transmitting capability of the optical means.

The alarm means is disposed at an opposite end of the light guide relative to the optical means. The alarm means includes an electrical circuit which is energized by the presence of the signal transmitted through the transmitter means. The alarm means, when energized, emits the alarm signal.

Many modifications and variations of the present invention will be readily apparent to those skilled in the art by a consideration of the detailed description con-

BRIEF DESCRIPTION OF THE DRAWINGS

Similar reference characters refer to similar parts throughout the figures of the drawings.

DETAILED DESCRIPTION OF THE DRAWINGS

Figure 1:
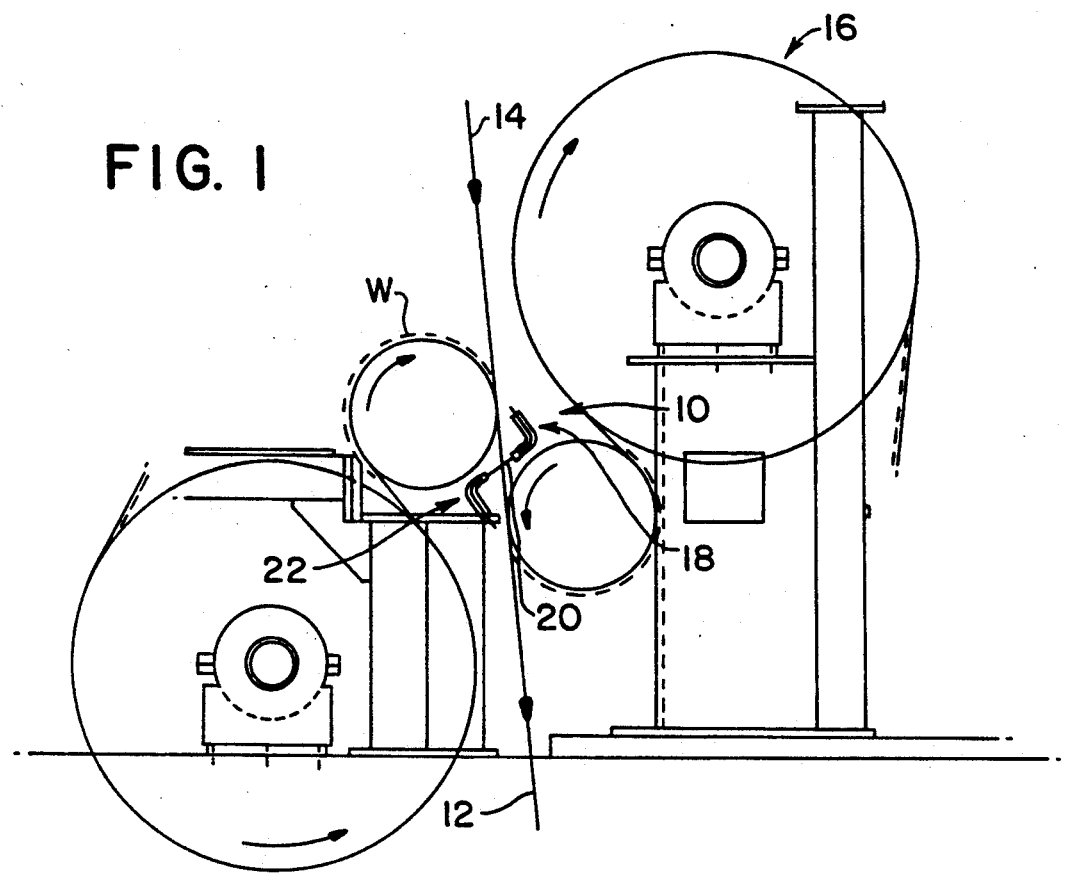
FIG. 1 is a side-elevational view of a sheet break detector apparatus according to the present invention for detecting a break in a sheet extending without open draw in a dryer section.

FIG. 1 is a side-elevational view of a sheet break detector apparatus, generally designated 10, for detecting a break in a sheet W disposed contiguously between an upstream and a downstream felt 12 and 14, respectively, of a paper machine dryer section, generally designated 16.

The apparatus 10 includes an infrared light emitter means, generally designated 18, which is disposed adjacent to the sheet W disposed between the felts 12 and 14 for emitting a beam 20 of infrared light towards the sheet W moving contiguously between the felts 12 and 14.

An infrared light receiver, generally designated 22, is disposed on an opposite side of the felts 12 and 14 relative to the emitter means 18 for receiving the beam 20 in the absence of the sheet W. The beam 20 is blocked by the presence of the sheet W, while the felts 12 and 14 permit the passage therethrough of the beam 20.

Figure 2:
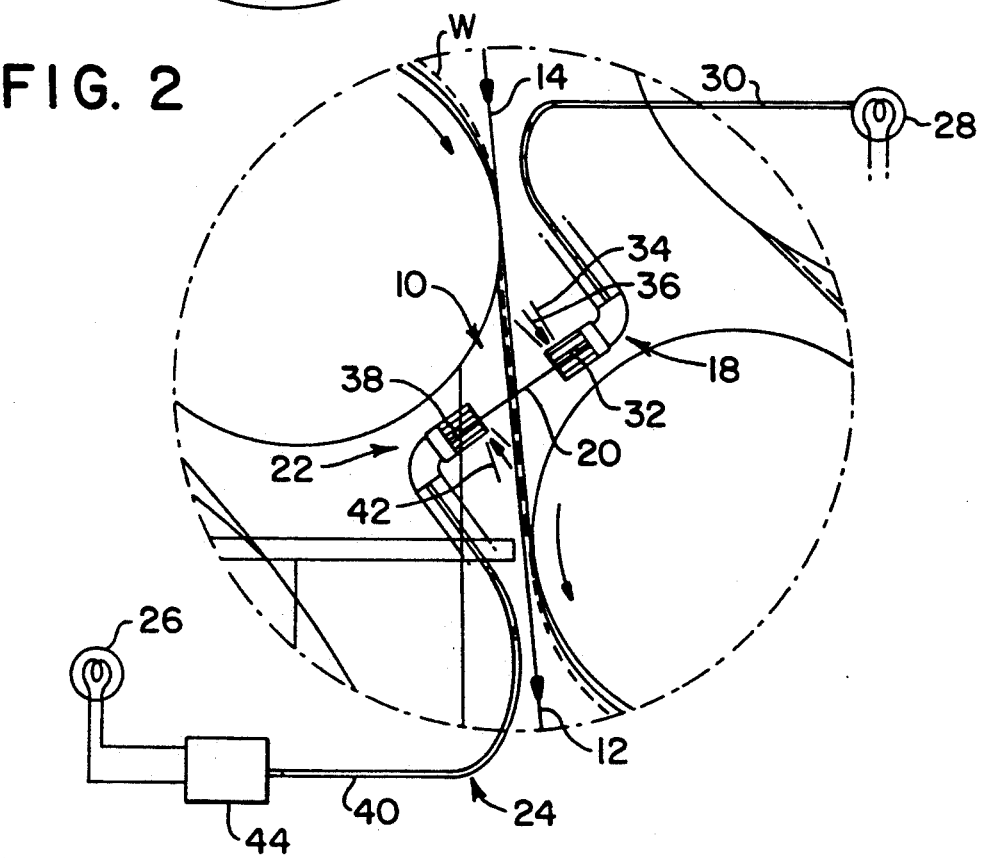
FIG. 2 is an enlarged view of the detector apparatus showing the disposition thereof adjacent the double-felted transfer section.

FIG. 2 is an enlarged view of the apparatus 10 and shows transmitter means, generally designated 24, connected to the receiver 22 for transmitting a signal from the receiver 22 in the absence of the sheet W.

Alarm means 26 are connected to the transmitter means 24 such that in the event of a sheet break, the beam of light 20 is received by the receiver 22, and the signal is transmitted to the alarm means 26 so that an alarm signal is generated, indicating that a sheet break has occurred.

The infrared light emitter means 18 includes an infrared light source generator 28 for generating infrared light. The emitter mean 18 also includes fiber-optic means 30 extending from the generator 28 for guiding the infrared light from the generator 28. The emitter means 18 also includes a lens 32 disposed at an opposite end of the fiber-optic means 30 relative to the generator 28 for concentrating the light generated by the generator 28

The detector apparatus 10 also includes air purge means 34 disposed adjacent to the lens 32 for directing a curtain of air, as indicated by the arrow 36, past the lens 32 for cleaning the lens 32.

The infrared light receiver 22 includes an optical means 38, such as an optical lens, for concentrating the beam 20 emitted from the emitter means 18, said beam passing through the felts 12 and 14 in the absence of the sheet W.

The transmitter means 24 includes a light guide 40 which is disposed closely adjacent to the optical means 38 for guiding the beam 20, which is concentrated by the optical means 38. The arrangement is such that the signal is a light signal which is transmitted in the absence of the sheet W between the felts 12 and 14.

The detector apparatus 10 also includes an air nozzle 42 which is disposed closely adjacent to the optical means 38 for blowing air across the optical means 38 in order to remove any contamination therefrom, thereby optimizing the light transmitting capability of the optical means 38.

The alarm means 26 is disposed at an opposite end of the light guide 40 relative to the optical means 38. The alarm means 26 includes an electrical circuit 44 which is energized by the presence of the signal transmitted through the transmitter means 24. The alarm means 26, when energized, emits the alarm signal.

The present invention provides a simple break detection means for detecting a break in a double-felted web transfer without open draw between adjacent dryer sections of a drying section. The detector apparatus, according to the present invention, is not dependent on the color of the felts or on the existence of a vacuum within one or more of the vacuum transfer rolls at the point of transfer of the web.

What is claimed is:

1. A sheet break detector apparatus for detecting a break in a sheet disposed contiguously between an upstream and a downstream felt in a without open draw transfer of a paper machine dryer section, said apparatus comprising:

an infrared light emitter means disposed adjacent to the sheet disposed between the felts for emitting a beam of infrared light towards the sheet moving contiguously between the felts, said emitter means being disposed on an opposite side of one of the felts relative to the sheet;

an infrared light receiver disposed on an opposite side of the felts relative to said emitter means for receiving said beam in the absence of the sheet, said beam being blocked by the presence of the sheet while the felts permit the passage therethrough of said beam;

transmitter means connected to said receiver for transmitting a signal from said receiver in the absence of the sheet; and alarm means connected to said transmitter means such that in the event of a sheet break, said beam of light is received by said receiver and said signal is transmitted to said alarm means so that an alarm signal is generated indicating that a sheet break has occurred such that scuffing between the felts is inhibited.

2. A sheet break detector apparatus as set forth in claim 1, wherein said infrared light emitter means includes:

an infrared light source generator for generating infrared light;

fiber-optic means extending from said generator for guiding said infrared light from said generator;

a lens disposed at an opposite end of said fiber-optic means relative to said generator for concentrating said light generated by said generator.

3. A sheet break detector apparatus as set forth in claim 2, further including:

air purge means disposed adjacent to said lens for directing a curtain of air past said lens for cleaning said lens.

4. A sheet break detector apparatus as set forth in claim 1, wherein said infrared light receiver includes:

an optical means for concentrating said beam emitted from said emitter means, said beam passing through the felts in the absence of the sheet.

5. A sheet break detector apparatus as set forth in claim 4, wherein said transmitter means includes:
a light guide disposed closely adjacent to said optical means for guiding said beam, which is concentrated by said optical means, so that said signal is a light signal which is transmitted in the absence of the sheet between the felts.

6. A sheet break detector apparatus as set forth in claim 5, further including:
an air nozzle disposed closely adjacent to said optical means for blowing air across said optical means in order to remove any contamination therefrom, thereby optimizing the light transmitting capability of said optical means.

7. A sheet break detector apparatus as set forth in claim 5, wherein said alarm means is disposed at an opposite end of said light guide relative to said optical means, said alarm means including:
an electrical circuit which is energized by the presence of said signal transmitted through said transmitter means, said alarm means, when energized, emitting said alarm signal.

8. A method of detecting a sheet break in a sheet disposed contiguously between an upstream and a downstream felt in a without open draw transfer of a paper machine dryer section, said method comprising the steps of:
directing a beam of infrared light from an infrared light emitter, the beam being directed towards the sheet supported between the felts, the beam being directed from an opposite side of one of the felts relative to the sheet;
detecting the beam by an infrared light receiver disposed on an opposite side of the felts relative to the emitter, the arrangement being such that the beam is detected in the absence of the sheet, the beam freely passing through the felts but being blocked by the presence of the sheet;
transmitting a signal from the receiver in the absence of the sheet; and
generating an alarm signal from an alarm connected to the transmitter, the beam of light being received by the receiver and the signal being transmitted to the alarm so that in the event of a sheet breakage, scuffing between the felts is inhibited.

* * * * *